United States Patent [19]

Rosskamp et al.

[11] 4,046,146

[45] Sept. 6, 1977

[54] APPARATUS FOR THE INHALATION OF MEDICINAL AGENTS

[75] Inventors: Gunter Rosskamp; Reiner Kolberg; Peter Gunzel; Hans-Jurgen Porep, all of Berlin, Germany

[73] Assignee: Schering Aktiengesellschaft, Berlin & Bergkamen, Germany

[21] Appl. No.: 606,737

[22] Filed: Aug. 21, 1975

[30] Foreign Application Priority Data

Aug. 22, 1974 Germany .............................. 2440623
June 2, 1975 Germany .............................. 2524902
June 30, 1975 Germany .............................. 2529522

[51] Int. Cl.$^2$ ............................................ A61M 15/00
[52] U.S. Cl. .................................... 128/266; 128/208; 222/193
[58] Field of Search ....................... 128/266, 206–211; 222/193, 370

[56] References Cited

U.S. PATENT DOCUMENTS

| 2,470,296 | 5/1949 | Fields | 128/206 |
| 2,587,215 | 2/1952 | Priestly | 128/206 |
| 2,901,150 | 8/1959 | Matter | 222/370 |
| 3,079,051 | 2/1963 | Clark et al. | 222/370 |
| 3,653,380 | 4/1972 | Hansen | 128/266 |
| 3,948,264 | 4/1976 | Wilke et al. | 128/208 |

Primary Examiner—Robert W. Michell
Assistant Examiner—Henry J. Recla
Attorney, Agent, or Firm—Millen & White

[57] ABSTRACT

Apparatus for the inhalation of medicinal agent is disclosed which comprises forming an aerosol, containing the medicinal agent, within a venturi tube-shaped interior configuration. The apparatus comprises a housing for receiving incoming air and combining the same with a medicinal agent passed from a container supported on the housing. The housing has a converging air inlet chamber in communication with an adjacent constriction. The constriction, in turn, communicates with an aerosol delivery section via a diverging diffuser chamber. The diffuser chamber may be part of the housing and the delivery section, which section provides for oral or nasal application may be attached thereto. In the alternative, the diffuser chamber and aerosol delivery section may comprise a single section integrally formed with the housing. The diffuser chamber, constriction and air inlet chamber cooperate to define the venturi tube-shaped configuration. Medicinal agent from the container enters the housing interior proximate the constriction, thoroughly combines with incoming air to form an aerosol, and exhausts through the aerosol delivery section.

15 Claims, 16 Drawing Figures

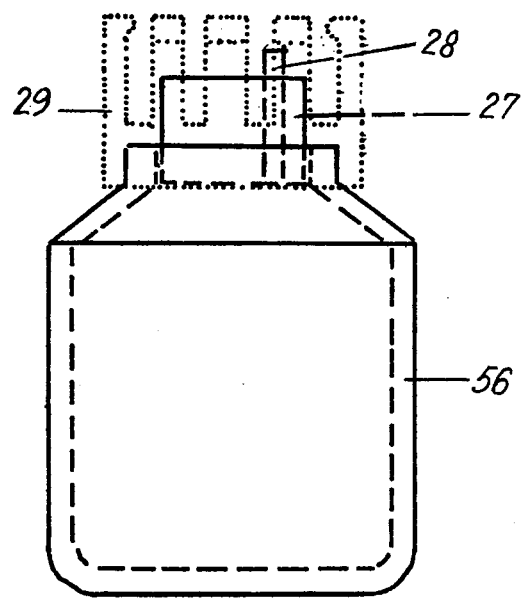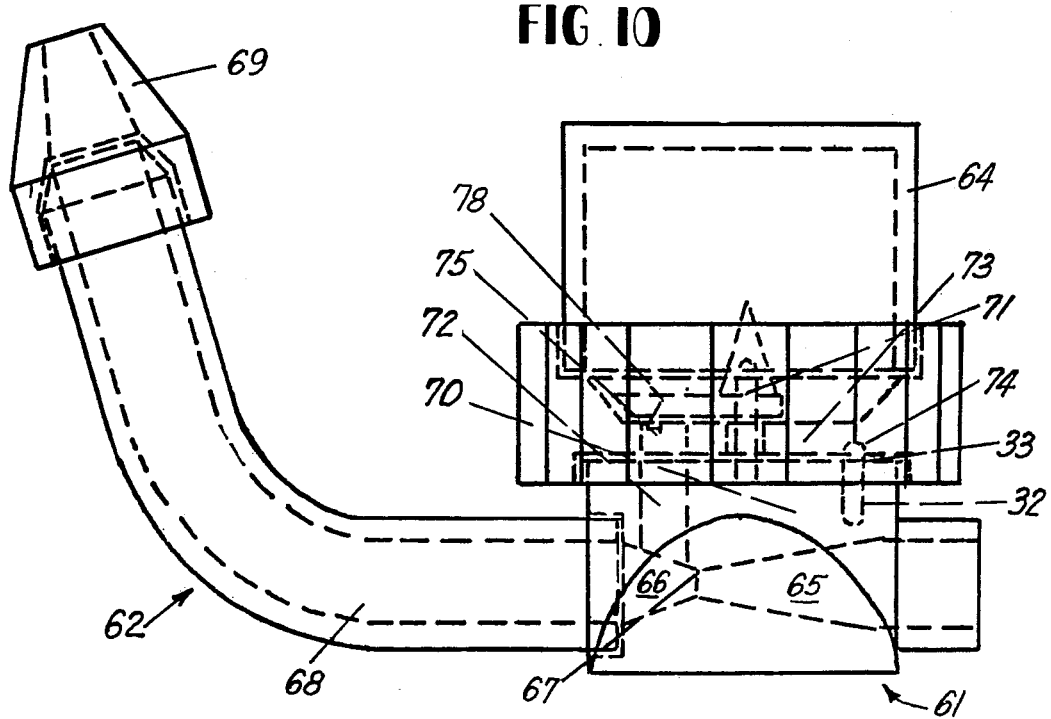

APPARATUS FOR THE INHALATION OF MEDICINAL AGENTS

BACKGROUND OF THE INVENTION

This invention relates to an apparatus for the inhalation of medicinal agents or drugs present in pulverulent or liquid form.

The administration of pulverulent or liquid medicinal agents by inhalation for the treatment of diseases of the respiratory tract, for example, bronchial asthma and rhinitis, is well known.

These medicinal agents can be administered by atomizing them with the aid of compressed air, hot steam, or a propellant gas to form a liquid or solid aerosol, and then inhaling the aerosol. This mode of administration, however, has the disadvantage that a predominant portion of the medicinal agent does not enter the respiratory tract. Consequently, an accurate dosing of the medicinal agent is impossible. Moreover, this mode of administration has the disadvantage that a considerable proportion of the drug enters the gastrointestinal tract and is absorbed therein, which can then cause undesired side effects. Moreover, when using propellant gases, the patient is subjected to the effects of the inhalation of an extraneous foreign substance.

In order to avoid this deficiency, devices have been developed for the inhalation of pulverulent medicinal agents in which the pulverulent drugs are atomized by the patient inhaling air through the device containing the drug. See, for example, Belgian Pat. No. 804,645 and U.S. Pat. No. 3,795,244.

These conventional devices possess movable, in most cases, propeller-type parts driven by the inhaled air, which effect an atomization of the pulverulent medicinal agents. The objective of conducting the pulverulent drug into the respiratory tract can be extensively attained by the use of these devices. Yet, these conventional instruments have several disadvantages.

First, since a considerable proportion of the inhaled air serves to set in motion the atomizing device, the patient must inhale very vigorously, which often causes considerable discomfort for the patient.

Second, adherence of a portion of the powdery drug to the movable parts of the device during inhalation is unavoidable, so that an accurate dosing of the drug is difficult.

Third, the manufacture of such devices with movable components renders them relatively expensive to the large number of people suffering from respiratory diseases.

Finally, such conventional devices have the disadvantage that only such pulverulent drugs can be used therein which are in perforated capsules, and proper dispensing of the drug from the capsules by these devices is assured only if the drug has a particle size large enough to permit the particles to be readily removed therefrom.

These conventional devices are thus unsuitable for dispensing pulverulent micronized or liquid medicinal agents.

It is an object of this invention to provide a dispensing device which does not have these disadvantages.

Upon further study of the specification and appended claims, further objects and advantages of this invention will become apparent to those skilled in the art.

SUMMARY OF THE INVENTION

The medicinal agent aerosol metering devices of this invention comprise an open-ended housing which defines a venturi tube-shaped interior configuration. The housing communicates with an aerosol delivery section which may or may not be formed integral with the housing. The delivery section may be either in the form of a mouthpiece or a nasal appliance. The housing also supports a container assembly for the medicinal agent to be dispensed. A passage in the apparatus extends from the medicinal agent supply through the container assembly and housing, and terminates upstream of the diffuser zone defined adjacent the throat of the venturi.

The various apparatus disclosed herein and embodying this invention make possible both the use of medicinal agents which are not encapsulated, as well as those having a certain particle size and disposed in perforated capsules, and also those which are pulverulent, micronized or liquid medicinal agents.

BRIEF DESCRIPTION OF THE DRAWINGS

In the drawings:

FIG. 9 is a front elevation view of a container employed with the apparatus of FIG. 8;

FIG. 10 is a front elevation view of a third alternative embodiment of an apparatus in accordance with the invention;

DESCRIPTION OF THE PREFERRED EMBODIMENTS

FIG. 1-6 illustrate one embodiment of an apparatus in accordance with this invention. Generally, the apparatus comprises a housing 1 having a venturi tube-shaped interior configuration therein. For purposes of this description, the venturi tube configuration discussed herein is thus understood to have a shape such that air flowing therethrough has approximately the same flow characteristic as is inherent in a gas flow through a venturi tube. Such a tube typically comprises an inlet chamber which converges to a narrow diameter throat or restriction. The tube also comprises an outlet chamber which diverges from the restriction to define a diffuser zone for the venturi tube.

The housing supports a container assembly 3 for the medicinal agent supply. A dispensing passage 5 extends from the medicinal agent through the assembly 3 and housing 1. Passage 5 terminates in the housing interior upstream of the diffuser zone to dispense medicinal agents into the housing and effect optimal liberation and subsequent atomization of the medicinal agent for inhaling purposes.

Figure 1:
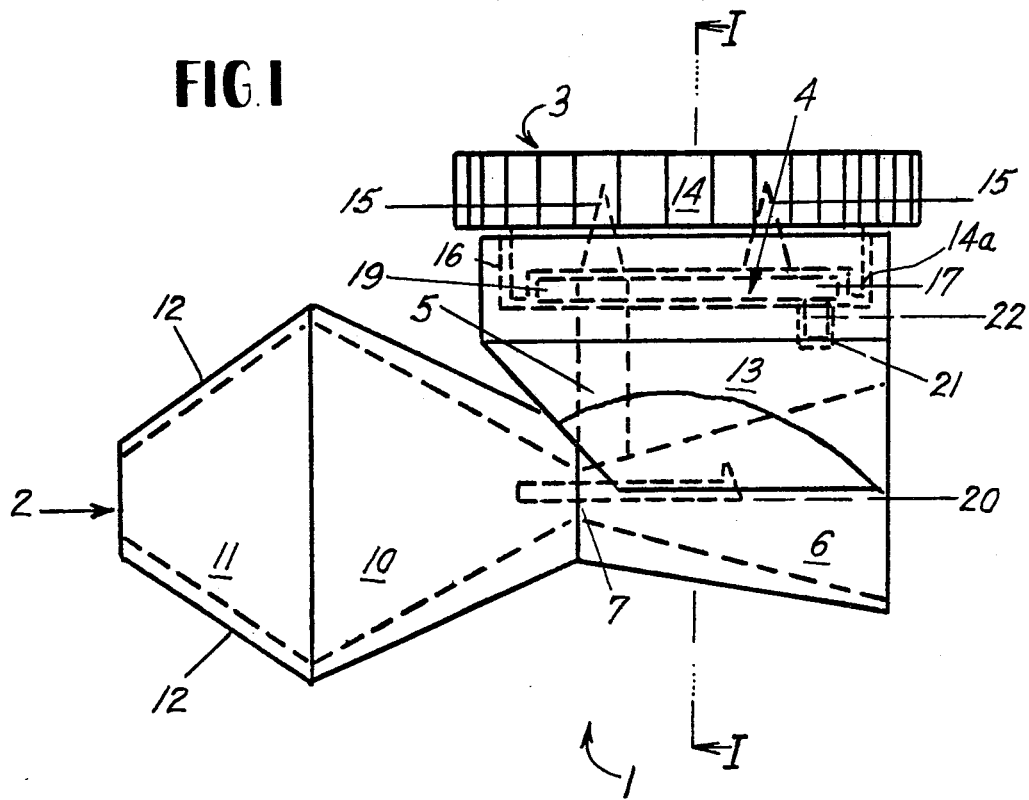
FIG. 1 is a front elevational view of one embodiment of an apparatus in accordance with the invention.
Figure 2:
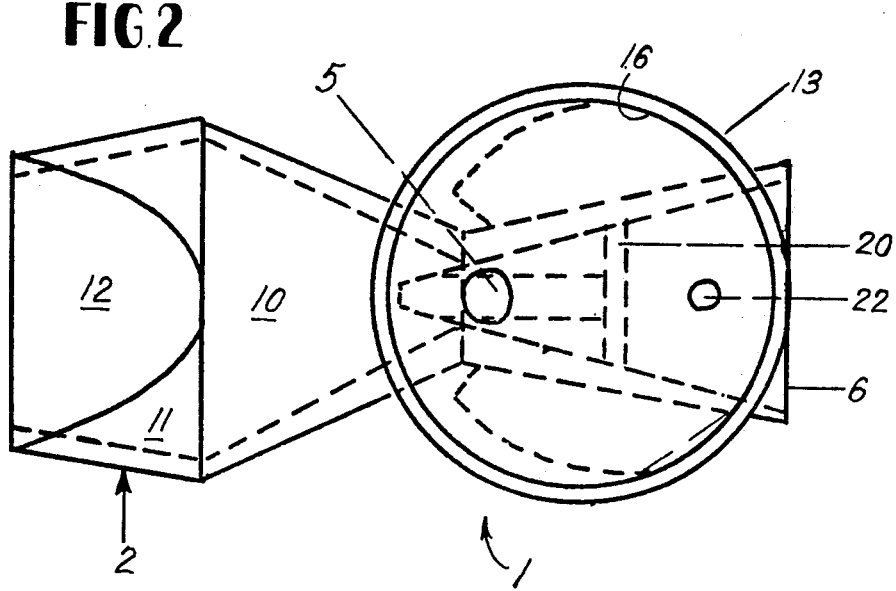
FIG. 2 is a plan view of the apparatus shown in FIG. 1, which the container removed.
Figure 3:
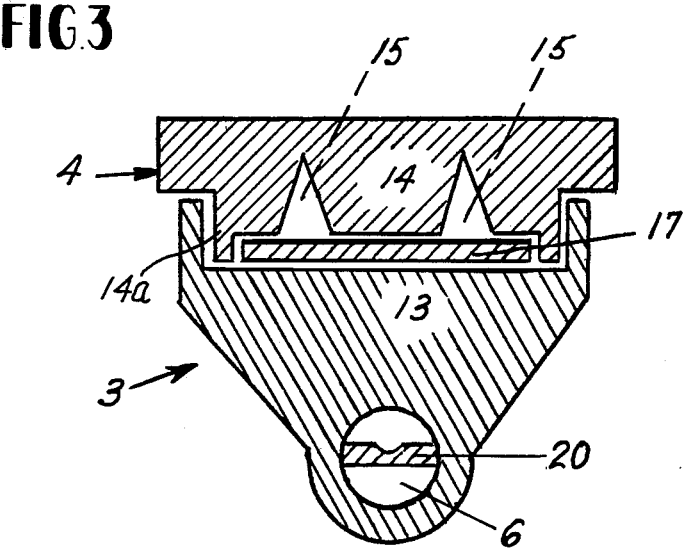
FIG. 3 is a full-section view along line I-I of FIG. 1.
Figure 4:
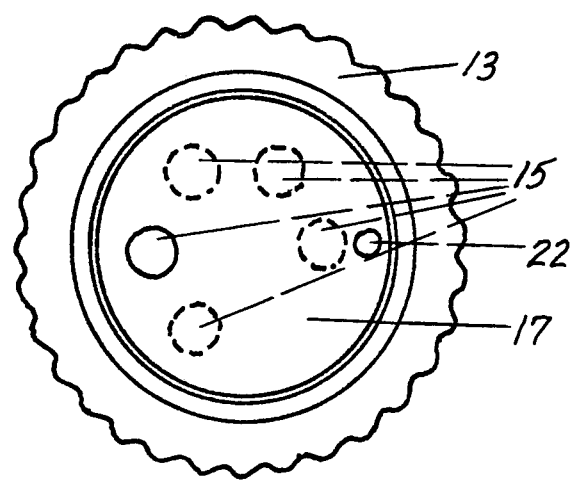
FIG. 4 is a bottom view of the container removed from the apparatus shown in FIG. 1.
Figure 5:
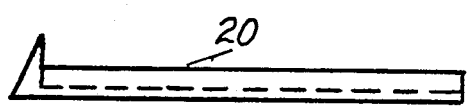
FIG. 5 is a front elevational view of the collecting plate employed in the apparatus shown in FIG. 1.
Figure 6:
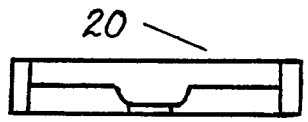
FIG. 6 is an end view of the collecting plate.

More specifically, the housing 1 of the apparatus shown in FIG. 1 comprises a pair of truncated cone-shaped shells which are joined together at their apices and which form an air inlet chamber 6 and a diffuser chamber 10. The chambers 6 and 10 communicate with each other through a narrow throat or construction 7. Chamber 6 can have a cylindrical, ellipsoidal, spherical, pear-shaped, or funnel-shaped form. Additionally, the air inlet opening of chamber 6 can comprise one or more openings dimensioned so that the maximum cross-sectional area of chamber 6 is about 1 to 100 times as large as the minimum cross-sectional area of the constriction 7. The chamber 6 preferably has a maximum internal diameter two to ten times as large as the minimum internal diameter of the construction 7.

To attain an optimum flow characteristic, the chamber 6 is suitably shaped so that it has a funnel-like configuration converging toward the construction 7 from its inlet opening.

The annular or tubular constriction 7 preferably has a length of 1 mm. to 20 mm. and has an internal diameter of 1 mm. to 5 mm. at its narrowest point.

The aerosol exhaust or delivery section 2 is disposed adjacent the chamber 10 and comprises a truncated cone shell 11 which serves as a mouthpiece and which is beveled on both its top and bottom surface 12 so that a quasi-rectangular or elliptical mouth opening is formed. This shaped of opening causes the user of the apparatus to unconsciously push his tongue underneath the exhaust section 2 to ensure optimal inhalation.

Alternatively, an aerosol exhaust section 62 (see FIG. 10) may be employed for nasal inhalation. Here, an upwardly bent applicator tube 68 is attached at one end to the diffuser chamber of the housing it is used with. The other end of the tube 68 carries a cap portion 69 having a shape suitable for nasal application. The cap may be a removable member, if desired.

The container assembly 3, for receiving and storing the medicinal agent, can be provided with a dose dispenser. The assembly 3 can be disposed on the housing 1 so that the dispensing passage 5, which terminates in the housing interior upstream of the diffuser zone, will extend directly through the assembly 3 and to the drug supply.

With this container assembly 3, it is possible to utilize a number of different types of containers 14 provided with dose dispensers, if the assembly 3 is provided with a container holder 13 which is fixedly mounted to the housing 1 and through which the aforementioned dispensing passage 5 extends. The configuration of the components cooperating to form the container assembly 3, e.g. container holder 13, drug container 14, and the dose dispenser, is dependent inter alia on wheather pulverulent or liquid drugs are to be administered with the aid of the apparatus of this invention.

A container assembly 3 for pulverulent medicinal agents can have the following structure. A drug container 14 is employed which is a cylindrical member having 2 to 24 cylindrical or conical bores 15. These bores 15 are disposed, preferably together with a blank zone, at equal radii from and symmetrically about the center of the cylinder. Each bore serves as a dose dispensing chamber. These chambers 15 each have an exactly defined content selected so that deired individual doses of the drug can be dispensed thereby. The container 14 can, if desired, be provided with a concentrically disposed cover disk 17 arranged thereon. Cover disk 17 has an opening 19 which makes it possible to dispense one drug dose at a time by providing that this opening 19 is arranged at the same distance from the center of the cover disk 17 as the bores 15 are from the center of the container 14. When using this container 14 and cover disk 17, the container holder 13 is provided with a cylindrical cavity 16 in which the container 14 and cover disk 17 are inserted and concentrically oriented with a depending flange 14a on the container at least partially encircling the disk. The cover disk 17 and the container holder 13 are provided with auxiliary locking means so that the cover disk 17 can be locked in place within the cavity 16. For example, a bore 21, disposed in the bottom of cavity 16 in diametric opposition to passage 5, will serve to receive an anchoring pin 22 for the disk 17. Passage 5 extends through the container holder 13 into the interior of the housing 1. The passage is disposed in the holder at the same distance from the center of the cavity 16 as the bores 15 are disposed from the center of the container 14. Thus, during the rotation of the drug container 14, dispensing of one drug dose at a time is possible.

By advancing the dosage chambers of the drug container 14, respectively, one of the dosage chambers 15 may then be located above the passage 5 in the container holder 13, while the remaining dosage chambers 15 are covered by the container holder 13, and by a cover plate 17 if one is employed. A collecting plate 20, shown specifically in FIGS. 5 and 6, may be disposed in the constriction 7 and underneath the dose dispensing passage 5, the plate 20 being so shaped that the drug exiting from the passage 5 is held on the collecting plate 20 even if the apparatus is held at an angle and is already subjected during inhalation, to a preliminary turbulence on this collecting plate, prior to the subsequent turbulence to which the drug is exposed in the diffuser zone. For this purpose, the collecting plate has a trough-like indentation in the longitudinal direction of the plate and has a front edge extending past the surface of the plate, forming an angle of 30° to 120° with the underside of the plate.

The described apparatus serves to administer a defined number of individual doses of a pulverulent medicinal agent. After the individual doses have been administered, the emptied container 14 is replaced by a new, drug-filled container. By such apparatus, it is possible to administer drugs, the use of which would be risky without exact control of the administered quantity.

Figure 7:
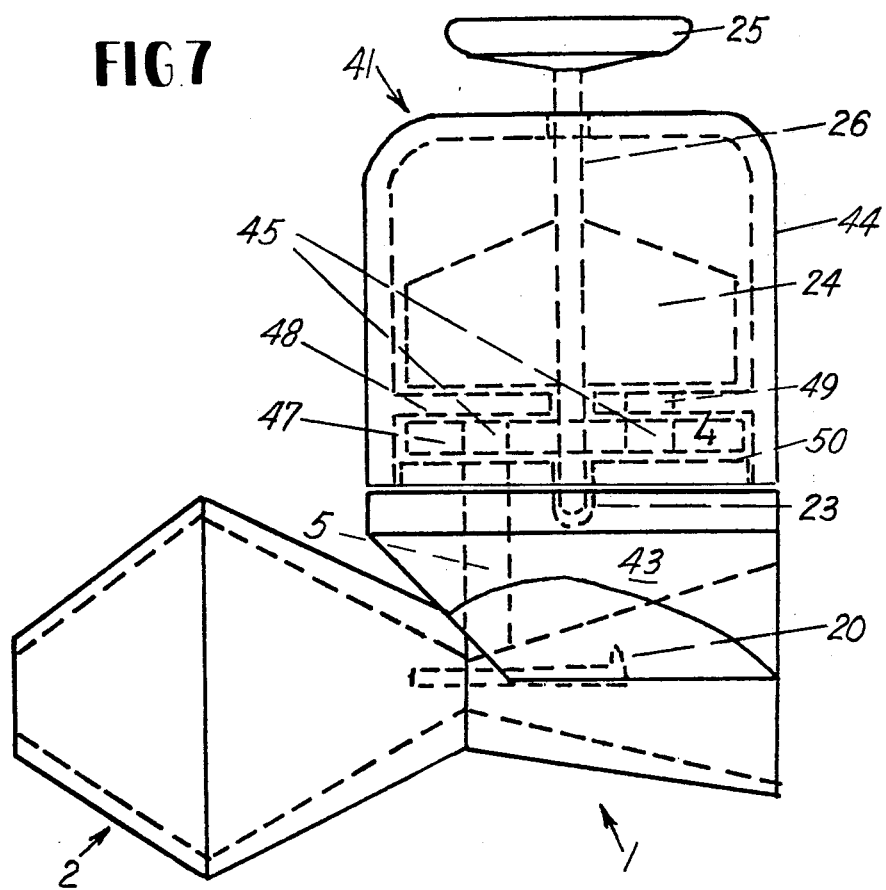
FIG. 7 is a front elevation view of a first alternative embodiment of an apparatus in accordance with the invention.

If it is desired to utilize the apparatus of this invention for the administration of a larger number of individual doses of a pulverulent medicinal agent than is possible with a single drug container 14, then a larger drug container in the shape of a bottle or can may be used. FIG. 7 illustrates an alternative embodiment of the invention employing such a large container.

A housing 1, aerosol exhaust section 2 and the collecting plate 20 are employed and are the same components with the same configuration and size as the corresponding components of the apparatus described in Example 1.

A drug container assembly 41 is provided which includes a container 44 having a dispensing device. The assembly comprises a drug container 44; a rod 26 provided with an agitator 24, and a handwheel 25; a dose dispensing plate 47, a cover 48; and a container holder 43.

A con-shaped drug container 44 may be employed which can be mounted to the container holder 43 which, in turn, is attached to the housing 1. Container 44 is sealed off on its underside by cover 48 having an opening 49 remote from the center of the cover. A movable rod 26 extending through the center of the drug container 44, and provided with a handwheel 25 and an agitator 24, is fixedly attached to a notable dose dispensing disk 47 concentrically disposed underneath the cover 48. The dose dispensing disk 47 has 1-20 dose dispensing chambers 45 spaced from the center of the disk 47 by the same distance as the distance of the opening 49 of the cover plate 48 from the center thereof.

The container holder 43 has a disk-shaped upper surface 50 with a disk dispensing passage 5 disposed therein at the same distance from the center of the upper surface 50 as the dose dispensing chambers 45 are from the center of the dose dispensing disk 47. The container holder 43 and/or the drug container 44 additionally comprise the customary annular or other locating means which make it possible to place the drug container 44 onto the container holder 43 so that the dose dispensing disk 47 likes concentrically on the disk-shaped surface 50 of the holder 43 and so that the opening 5 of the holder and the aperture 49 of the cover are mutually offset.

By rotating the handwheel 25 and thus rotating the dose dispensing disk 47, one dose dispensing chamber 45 at a time can pass over the passage 5 in the container holder 43 and underneath the cover 48, while the remaining dose dispensing chambers 45 are closed off by the container holder 43.

Figure 11:
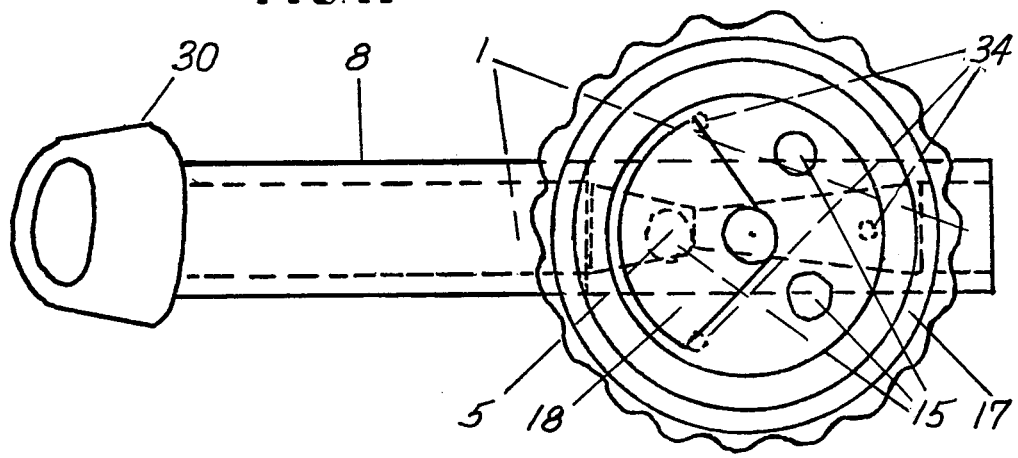
FIG. 11 is a plan view of the apparatus shown in FIG. 10 with the drug container being removed.

Another possible embodiment of the apparatus described above can be as follows, for example:

FIGS. 10 and 11 illustrate an alternative embodiment, described more fully in Example 4, where a support 70 disposed on a housing 61 has a disk-shaped top surface. A pin 71 is mounted to the center of the top surface. A dispensing passage 72 which extends from the housing interior through the housing 61 and support 70, terminates in the top surface displaced from the pin 71. A dose dispensing disk 73 is rotatably, centrally disposed on the pin 71. Disk 73 is provided with 1-20 bores defining disk dispensing chambers 75 disposed the same distance from the center of the disk 73 as the passage 72 is from the center of the disk-shaped top surface of the support 70. The dose dispensing disk 73 is provided with a holding ring on which a can-shaped drug container 64 can be placed. A cover 78 is rigidly attached to the pin 71. Cover 78 is of such a configuration that it covers a disk dispensing chamber 75 disposed above the passage 72 with respect to the content of the drug container 64.

All the aforedescribed devices can be provided with the customary auxiliary means acting so that the container assembly or the dose dispensing plate, during turning, are locked in position each time a dose dispensing chamber is disposed above the passage 5.

Figure 8:
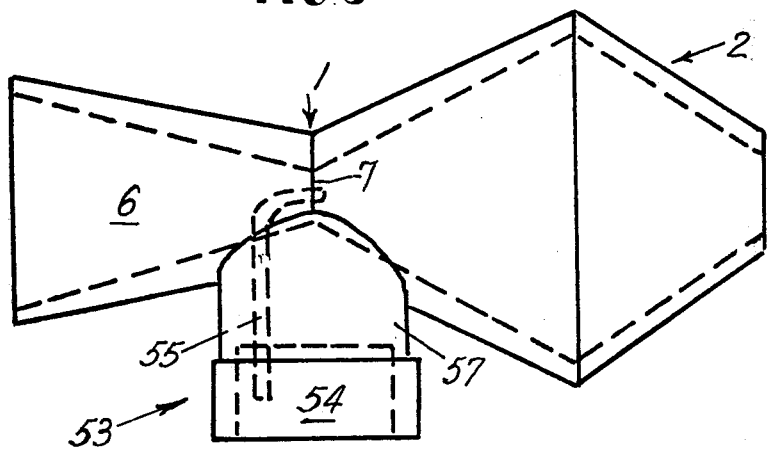
FIG. 8 is a front elevation view of a second alternative embodiment of an apparatus in accordance with the invention.

Apparatus embodying this invention and intended to dispense a liquid medicinal agent is shown in FIGS. 8 and 9. Such apparatus includes a housing 1, having an aerosol exhaust section 2. The housing 1 and aerosol exhaust section 2 have the same configuration and size as the corresponding elements of the apparatus described in Example 1. Housing 1 is connected with a liquid container holder 53 which includes a cylindrical cavity 54, serving as a dose dispensing chamber. Holder 53 supports a tubular dispensing member 55 which extends into the cavity 54. By means of a conventional mounting element, a bottle-shaped drug container 56 formed of an elastic material can be placed on the holder 53. This drug container 56 is sealed by a plug 27 through which a tube 28 extends, when the container 56 is attached into the cavity 54 of the holder 53.

In another group of related embodiments, the container housing for the medicinal agent can be open on both sides and can be arranged so that the dispensing opening for the container terminates directly in front of the diffuser zone of a housing have a venturi-shaped interior configuration. The container can be tubular, funnel-shaped, conical, or pear-shaped and is provided at two ends with one or more openings. The container can also be provided internally with webs, knobs, or bulges, which are advantageous particularly if the apparatus is to serve for using medicinal agents housing in capsules. One such embodiment, shown in FIG. 13, comprises a unitary structure including a container 83 for medicinal agent which is interposed between an air inlet chamber 86 and a construction 87 with which container 83 is in direction communication. An aerosol exhaust section 82 is also provided.

Figure 14:
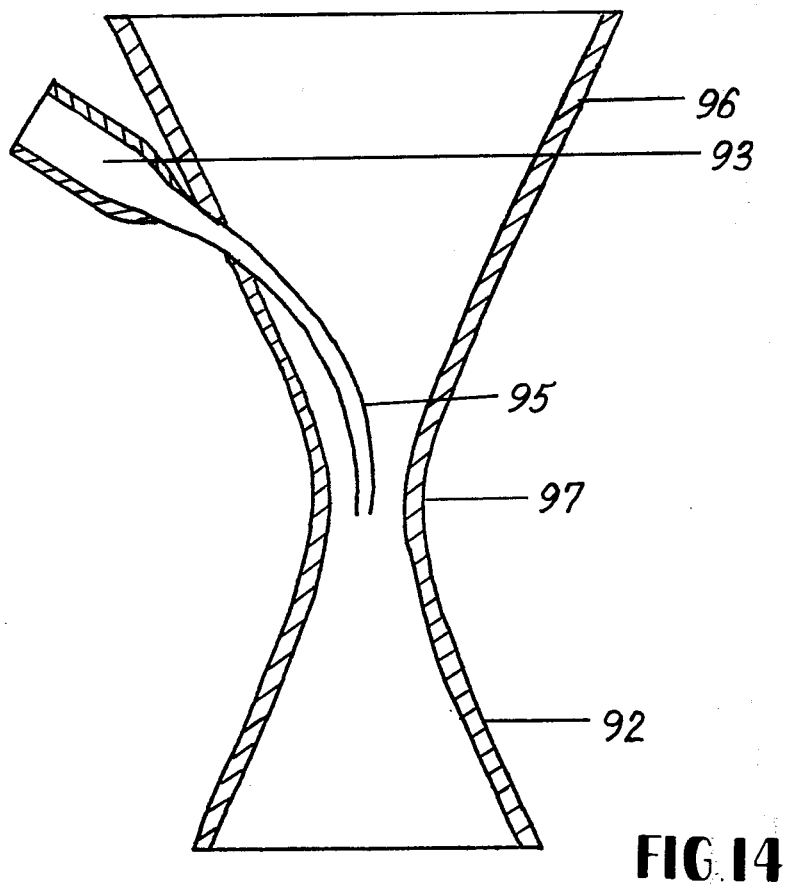
FIG. 14 is a front elevation view, in full section, of a sixth alternative embodiment of an apparatus in accordance with the invention.
Figure 15:
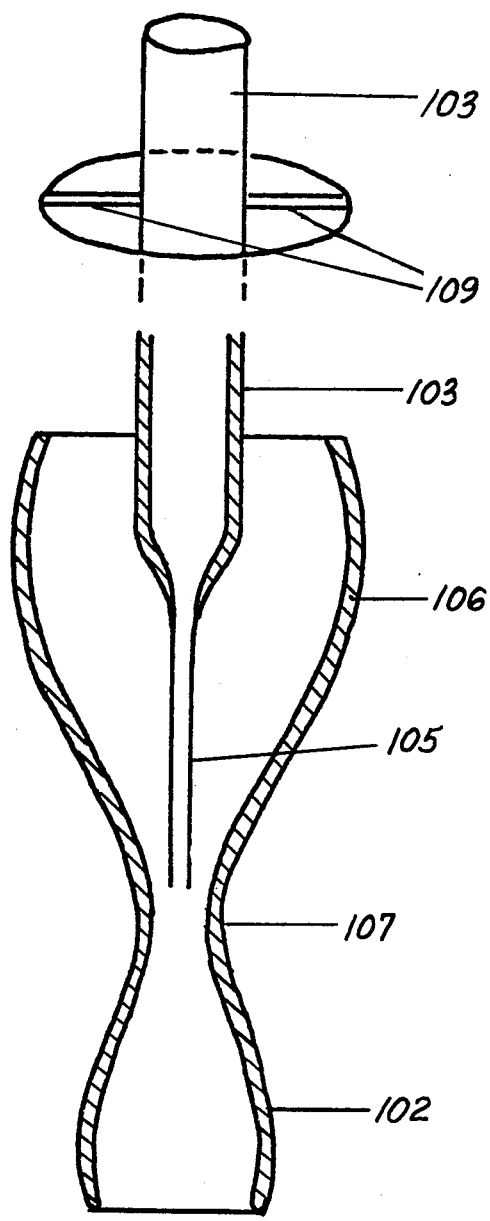
FIG. 15 is a front elevation view, in partial section, of a seventh alternative embodiment of an apparatus in accordance with the invention.

If this container 83 contains encapsulated drugs, then it will have an internal diameter 1.0 – 2.0 times as large as the capsule diameter and a length which is 0.6 – 1.2 times as large as the length of the capsule to be introduced therein. Two other such embodiments are shown in FIGS. 14 and 15. In each of those embodiments, the housing supports a funnel-like container for receiving the drugs. The container is provided with a capillary-type outlet having an opening which terminates in or immediately upstream of the housing's construction. The capillary-type outlet of this container suitably has an inside opening of 0.1 mm. to 2 mm. In the embodiment shown in FIG. 15, outlet 95 can extend in a straight line, wherein the funnel 93 (suitably provided with a tubular extension) is arranged in the center of the chamber 96 of housing 91 and is joined therewith by means of webs 99.

In the embodiment shown in FIG. 14, the capillary-type outlet 85 can be curved, and the funnel 83 can be attached laterally to the wall of chamber 86 so that it extends thereinto from the outside.

Both containers 83 and 93 are suitably dimensioned so that they are suitable for receiving either a drug capsule or 1 mg. to 1000 mg. of pulverulent or liquid medicinal agent.

Figure 13:
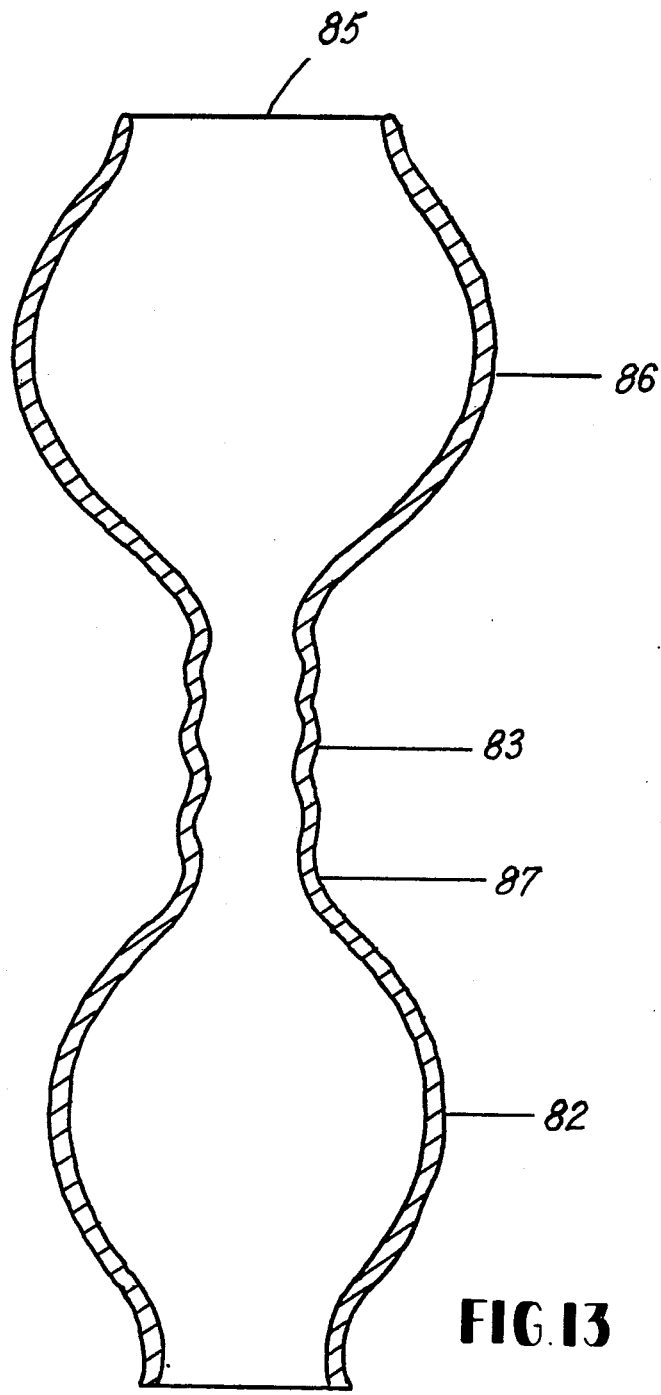
FIG. 13 is a front elevational view, in full section, of a fifth alternative embodiment of an apparatus in accordance with the invention.

The material of which the apparatus in FIGS. 13–15 is manufactured is of no importance for the mode of operation of the apparatus. The latter can be made of glass, a ceramic material, a synthetic resin, or a metal. To ensure simple manufacture of the apparatus, it is advantageous to make the apparatus of a readily processable plastic.

In order to make it possible for the patient to control the inhaling process, it is suitable to make the apparatus of a transparent, optionally slightly colored synthetic resin.

To avoid electrostatic charging of the apparatus, the housing can optionally be provided with a conductive coating, or it can be made of a synthetic resin mixed with a conductive implant.

It is obvious to a person skilled in the art that the apparatus of this invention can additionally be equipped with auxiliary means which, if necessary, facilitate the use of the apparatus. Thus, auxiliary devices can, for example, be connected to the air inlet chamber 6 of the housing, making it possible to effect an inhalation with the aid of compressed air, a propellant gas, or hot steam. On the other hand, the apparatus can also be additionally equipped with needle-shaped or blade-like components arranged so that they perforate a drug capsule introduced into the apparatus.

Without further elaboration, it is believed that one skilled in the art can, using the preceding description, utilize the present invention to its fullest extent. The following examples, which describe specific apparatus embodying the invention disclosed herein, are, therefore, to be construed as merely illustrative, and not limitative of the remainder of the disclosure in any way whatsoever.

EXAMPLE I

This apparatus, as seen in FIGS. 1-6, comprises a housing 1 having a venturi tube-shaped interior configuration. The apparatus also comprises a container holder 13, a collecting plate 20, a cover disk 17, and a drug container 14, each of which are manufactured of a thermoplastic, transparent, light-green synthetic resin.

The housing 1 forms the air inlet chamber 6 and the diffusion chamber 11. Between chambers 6 and 11 is a constriction 7 having an internal diameter of 4 mm. The apparatus also includes an aerosol delivery section 2 in the form of a truncated cone 11 bounded on the topside and underside by cover plates 12 so that a quasi-rectangular mouth opening is formed having a height of 6 mm. and a length of about 20 mm. A wedge-shaped collecting plate 20, having a thickness of 2 mm. and a length of 17 mm., is horizontally disposed within the housing so that the plate extends 12 mm. into the chamber 6 and terminates flush with the sidewalls thereof. This collecting plate has a front edge beveled toward its bottom surface and a groove on its top surface.

The container holder 13 is disposed over the chamber 6 so that its bottom surface contacts the top half of the chamber 6 flush. The top of holder 13 is a cylindrical cavity 16 having an annular rim. A passage 5, having a diameter of 3.5 mm., is provided in the holder 13. The canter of passage 5 is positioned 6 mm. from the center of the cylindrical cavity 16. Passage 5 extends through the container holder 13 into the chamber 6 and terminates directly at the construction 7.

The container 14, for the medicinal agent, is cylindrical in shape. It has an annular rim with a knurled side edge. It also has a cylindrical recess on its bottom surface (See FIG. 3). Five conical bores 15 are disposed in the recess, offset from one another by 60° and being disposed 6 mm. from the center of the recess. These bores, which serve dosage as dosage chambers, have a height of 8 mm. and their bottom openings have a diameter of 3.5 mm.

A cover disk 17 is loosely inserted in the recess of the container. This disk has an opening 19 with a diameter of 3.5 mm. disposed at a distance of 6 mm. from the center of the disk 17. This disk 17 supports an anchoring pin 22 remote from the disk's opening.

To operate this device, the container 14, provided with the cover disk 17 and filled in each of the conical bores with 20 mm$^3$ of a pulverulent drug, is inserted in the container holder 13 so that the holding pin 22 of the cover disk 17 locks in the bore 21. By rotating the container 14 in 60° intervals, from one chamber 15 to the next, with each such rotation, 20 mm$^3$ of medicinal agent is liberated and can be inhaled.

EXAMPLE 2

The apparatus depicted in FIG. 7, as noted previously, comprises a housing 1, having a venturi tube-shaped interior configuration and equipped with an aerosol exhaust section 2, and a collecting plate 20. The apparatus also comprises a container assembly 41 provided with a dispenser device 42. All the components are manufactured of polycarbonate.

The container holder 43 of this device differs from the one described in Example 1 in that the holder's cylindrical disk surface has an annular recess and central bore 23 instead of an annular rim and an offset bore 21.

The drug container 44 of the container assembly 41 is a hollow cylinder closed off at the top and provided with a cover 48 for its bottom surface. The cover 48 is mounted in the drug container 44 so that the container has a 6 mm. high vertical rim extending below the cover 48. A central aperture is provided in cover 48. The rod 26 extends through the top surface and interior of container 41 and through the aperture in cover 48. Rod 26 supports handwheel 25 above the container and helically twisted agitator 24 within the container. At a distance of 6 mm. from the center of the cover, the latter has an opening 49 with a diameter of 3.5 mm. In close proximity, underneath the cover 48, the rod 26 supports dose dispensing disk 47 having a thickness of 2.6 mm. This dose dispensing disk has two dose dispensing chambers 45 each having a diameter of 3.5 mm., diameterically disposed at a distance of 6 mm. from the center of the dose dispensing disk.

To operate the device, the container assembly 3, filled with a pulverulent drug, is placed on the container holder 13 so that the bore of the cover 48 is aligned with the passage 5 of the container holder 43 serving for dispensing purposes. By turning the handwheel in 180° intervals, advancing from one chamber 45 to the next, with each such rotation, 25 mm$^3$ of medicinal agent pass into the passage 5 and can be inhaled.

EXAMPLE 3

This apparatus provides for the inhalation of liquid drugs.

FIG. 8 shows a housing 1, having a venturi tube-shaped interior configuration, and an aerosol exhaust section 2. A container holder 53 is also provided. These components are made of polycarbonate.

The container holder 53 includes a hollow cylinder or cavity 54. Cylinder 54 has a height of 9 mm. and an internal diameter of 12 mm. This cylinder 54 is supported by a base 57 anchored to the housing 1 so that the center of the hollow cylinder is arranged above the constriction 7 of the housing 1. Metal tube 55, having an internal diameter of 1 mm. is located at a distance of 4 mm. from the center of the hollow cylinder. This metal tube extends 3.5 mm. into the hollow cylinder. Tube 55, which also extends through the base 57 and chamber 6, is curved within the chamber 6 so that it extends through the center of the construction 7 and terminates 1 mm. behind the constriction 7.

FIG. 9 shows the container 3 for the apparatus of FIG. 8. This container consists of the medicine bottle 56, made of polyethylene, with 10 ml. capacity. In the bottleneck of the medicine bottle 56, a plug 27 of polyethylene is arranged so that it projects 5 mm. past the rim of the bottle. At a distance from the center of the plug, a metal tube 28 having an internal diameter of 1 mm. extends through the plug and projects 3.5 mm. there beyond.

Above the neck of the bottle, an annular holder 29 provided with eight hook like projections is arranged. Holder 29 is made of an elastic synthetic resin.

To use the apparatus in FIGS. 8 and 9 the housing 1 is connected with the container 56, and the cavity 54 is filled by means of pressure applied to the liquid filled container 56. Then, the pressure is released and the drug present in the cavity 54 is inhaled.

EXAMPLE 4

The apparatus shown in FIGS. 10 and 11 comprises a housing 61 having a venturi tube-shaped interior configuration. The housing 61 is connected to an aerosol exhaust device 62 for use as a nasal applicator. Housing 61 supports a container assembly 63 which includes a drug container 64 having a dose dispenser. All of these components are manufactured from a thermoplastic, transparent synthetic resin.

The housing 61 is a tubular structure which has cone shaped air inlet and diffuser chambers, 65 and 66, respectively, joined at their apices and communicating thereat through a constriction 67. Constriction 67 has a diameter of 2 mm. and is positioned 22 mm. downstream of the inlet opening of the chamber 65. The aerosol exhaust device comprises an applicator tube 68 attached to the housing 61, adjacent chamber 66, and bent upwardly, as can be seen from FIG. 10. The end of the applicator tube 68 is beveled and carries a detachable, conical cap 69 provided with a perforation.

The container assembly 63 includes a disk-shaped support 70 disposed on the housing 61, so that the central axis of the support 70 is disposed 4 mm. upstream of the constriction 67. In the center of the support 70, a pin 71 is mounted, projecting beyond the plate. At a distance of 6 mm. from its center, the support 70 has a passage 72, having a diameter of 3.5 mm., which terminates in the diffuser chamber 66 of the housing 61. A recess 32 is disposed in the support 70 in diametric opposition to passage 72. A coil spring, with a locking pin 33 attached thereto, is disposed in this recess. A dose dispensing disk 73 is rotatably disposed on the support 70. Dispensing disk 73 is provided with a central aperture as well as three bores 75, which serve as dosage chambers. All three bores 75 have a diameter of 3.5 mm. Each bore 75 is located 6 mm. from the center and is offset with respect to the other bores by 120°. The underside of the dispensing disk 73 carries three hemispherical indentations 74, each disposed opposite to the bores 75 and each being at a distance of 9 mm. from the center of disk 73. The pins 33 can engage these indentations 74.

A cover 78, fixedly attached to the pin 71, is disposed adjacent to and above the disk 73. Cover 78 closes off the bore 75, located above the passage 72, with respect to the drug container 64.

The drug container 64 itself is a can-shaped component which can be attached to the dispensing disk 73. This embodiment permits inhaling of 20 mm$^3$ doses of a pulverulent medicine.

EXAMPLE 5

Figure 12:
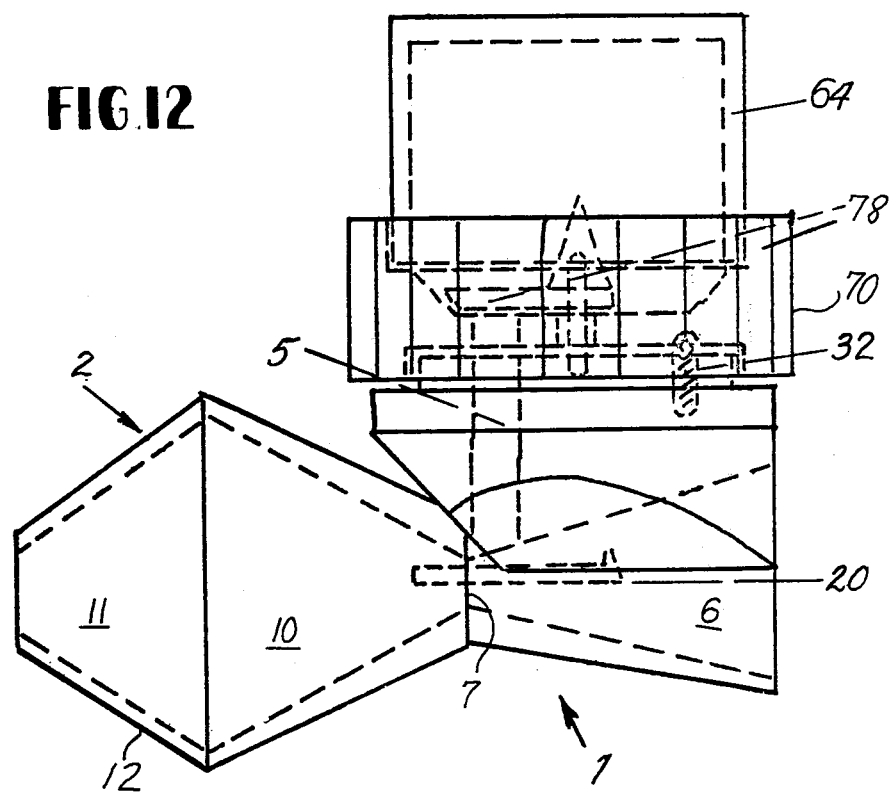
FIG. 12 is a front elevation view of a fourth alternative embodiment of an apparatus in accordance with the invention.

The apparatus shown in FIG. 12 consists of a housing 1, an aerosol exhaust section 2, and a collecting plate 20, all of which have the same configuration as similarly numbered components described in Example 1. The remaining components of the apparatus shown in FIG. 12 have the same configurations as similarly functioning components shown in FIG. 10.

EXAMPLE 6

This apparatus, shown in FIG. 13, is made of a transparent glass. It is 90 mm. in length and comprises a spherical aerosol exhaust section 82, having a maximum internal diameter of 25 mm. and a circular opening with a diameter of 20 mm. A constriction 87, having an internal diameter of 5 mm. is interposed in communication with and between the aerosol exhaust section 82 and a tubular drug container 83 housing the pulverulent medicinal agent. Container 83, with a length of 20 mm. and a minimum internal diameter of 6 mm., has three annular bulges for holding encapsulated drugs.

Container 83 is connected to a pear-shaped air inlet chamber 86 having a length of 40 mm. and a maximum internal diameter of 25 mm. Chamber 86 is provided with a circular air inlet opening 85.

The above-described apparatus can also be structured so that it uses either of the aerosol exhaust sections, 2 or 62, described in Examples 1 and 4, respectively.

This apparatus is preferably utilized for inhaling pulverulent medicinal agents disposed in a perforated drug capsule having a diameter of 6 mm. and a length of 18 mm. The capsules are introduced into and retained within the container 83 for inhaling purposes.

EXAMPLE 7

This apparatus, shown in FIG. 14, is made of glass. The housing consists of a funnel-shaped aerosol exhaust section 92 having a length of 25 mm. and a maximum internal diameter of 25 mm., a constriction 97 having a minimum internal diameter of 5 mm., a funnel-shaped air inlet chamber 96 having a length of 35 mm. and a maximum internal diameter of 38 mm.

A second glass tube having an inside diameter of 6 mm. serves as the container 93 to housing the medicinal agent. This tube extends unchanged for 13 mm., then it narrows in the manner of a funnel and is drawn out into a capillary 95 having an inner diameter of 1 mm. and a length of 25 mm., bent by an angle of about 120°.

Container 93 is inserted in an opening of the housing and bonded thereto by melting so that the opening of the capillary is coaxially aligned with the longitudinal axis of the constriction 97.

The above-described apparatus can also be constructed so that it has, in place of the exhaust section 92, an exhaust section as disclosed in either Example 1 or 4.

This apparatus is preferably used for the inhalation of pulverulent and liquid medicines present in a storage vessel equipped with metering means.

EXAMPLE 8

This apparatus, manufactured of "Plexiglas", is shown in FIG. 15.

The apparatus comprises a funnel-shaped aerosol exhaust device 102 having a length of 20 mm. and a maximum internal diameter of 13 mm. Exhaust device 102 is connected with in approximately tubular constriction 107 having a length of 4 mm. and an inner diameter of 4 mm.

This constriction 107, in turn, is in communication with a pear-shaped air inlet chamber 106 having a length of 30 mm. and an inner maximum diameter of 25 mm. At its air inlet opening, this chamber has a circular opening having a size of 23 mm., interrupted by two mutually symmetrical webs 109 leading to the center of the opening. These webs support a drug container 103, having a length of 41 mm. and an inside diameter of 6 mm. Container 103 is tubular and is disposed on the axis of symmetry of the apparatus. At its downstream end, the container has a funnel-shaped constriction terminating in a capillary 105 having an inside diameter of 1 mm., and being of sufficient length that it extends into the center of the constriction 107.

This apparatus is adapted for inhaling pulverulent drugs housed in a perforated capsule having a length of 18 mm. and a diameter of 6 mm.

EXAMPLE 9

Figure 16:
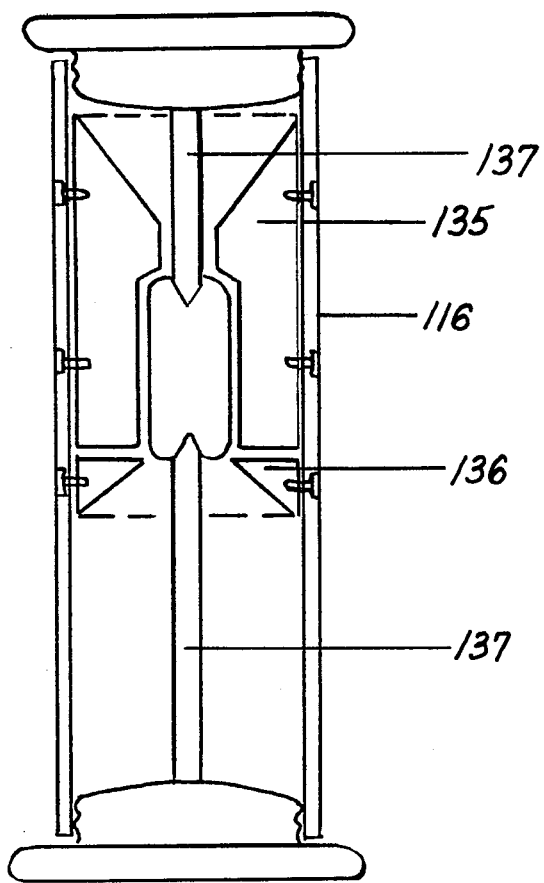
FIG. 16 is a front elevation view, in full section, of an eighth alternative embodiment of an apparatus in accordance with the invention.

This apparatus, illustrated in FIG. 16, is made of polyvinyl chloride. It comprises a tube 116 having a length of 60 mm., an external diameter of 21 mm., and an internal diameter of 19 mm. A drum-shaped component 135, having a length of 25 mm. is inserted fully into and supported at one end of the tube. Component 135 is provided with a central bore having a length of 13 mm. and a diameter of 8 mm., extending from its inner end. A smaller central bore extends through the entire component 135 and has a diameter of 4 mm. A funnel-shaped opening is disposed at the outer end of component 135.

A drug capsule, having a diameter of 6 mm. and a length of 12 mm. is introduced into the large bore of component 135. Then, a funnel-shaped capsule holder 136 is inserted into the tube 116, and the arrangement is closed at each end with one plug. Each plug carries a needle 137 having a diameter of 2 mm. and a length such that, when the plug is inserted into tube 116, it penetrates the capsule.

After removal of the plug, the drug present in the device can be inhaled. After use, the device is discarded.

From the foregoing description, one skilled in the art can easily ascertain the assential characteristics of this invention, and without departing from the spirit and scope thereof, can make various changes and modifications of the invention to adapt it to various usages and conditions.

What is claimed is:

1. Apparatus for the inhalation of medicinal agents in pulverulent form, comprising a housing having a venturi tube-shaped interior configuration including a diffuser zone and provided with an aerosol exhaust section; said housing including a dispensing opening having a delivery end which terminates upstream of the diffuser zone of the venturi-like housing, a container for the medicinal agent, means mounting said container on said housing for dispensing of the medicinal agent to said dispensing opening, and a collecting plate adjacent the delivery end of said dispensing opening and disposed longitudinally and transversely in close proximity to the venturi tube-shaped interior configuration of the housing.

2. Apparatus according to claim 1, wherein said container for the medicinal agent is provided with a dose dispensing device and is attached to the housing so that the passage from the dose dispensing device terminates within the housing upstream of the diffuser zone.

3. Apparatus according to claim 2, wherein said housing has an air inlet chamber with an air inlet opening at its upstream end, said chamber in communication at its downstream end with a tubular constriction; said constriction being, in turn, in communication with said aerosol exhaust section.

4. Apparatus according to claim 3, wherein said air inlet chamber is a funnel-shaped member having an open upstream end from which said chamber converges inwardly.

5. Apparatus according to claim 4, wherein said container for the medicinal agent is disposed between said air inlet chamber and said constriction, said container having a tubular shaped.

6. The apparatus claim 5, wherein the interior of said container includes means for retaining medicinal agent therein.

7. Apparatus according to claim 4, wherein said container includes a dose dispensing device and a container holder fixedly joined to said housing.

8. Apparatus according to claim 7, wherein said container for the medicinal agent is provided with 2-24 dose dispensing chambers, said container being movable mounted on said container holder.

9. Apparatus according to claim 7, wherein a dose dispensing plate is movably mounted between said container holder and said container for the medicinal agent, said dose dispensing plate having 1-20 dose dispensing chambers.

10. Apparatus according to claim 1, wherein said aerosol exhaust section has a transversely elongate opening, said section initially diverging outwardly and then coverging.

11. Apparatus according to claim 1 wherein the dose dispensing opening is selectively opened and closed by movable means adjacent the upper end thereof.

12. Apparatus according to claim 11, wherein the interior housing configuration provides an air inlet opening at its upstream end and a downstream aerosol exhaust section communicating with the inlet opening through a tubular constriction transversely of which the collecting plate is mounted with its delivery end at the upstream end of the aerosol exhaust section.

13. Apparatus according to claim 12 wherein the collecting plate is substantially triangular with the longitudinal edges disposed along the adjacent surfaces of the air inlet opening.

14. Apparatus according to claim 13 wherein the collecting plate is longitudinally troughed.

15. Apparatus according to claim 14 wherein the delivery end of the dose dispensing opening is at the upstream side of the tubular constriction.

* * * * *